Figure 1:
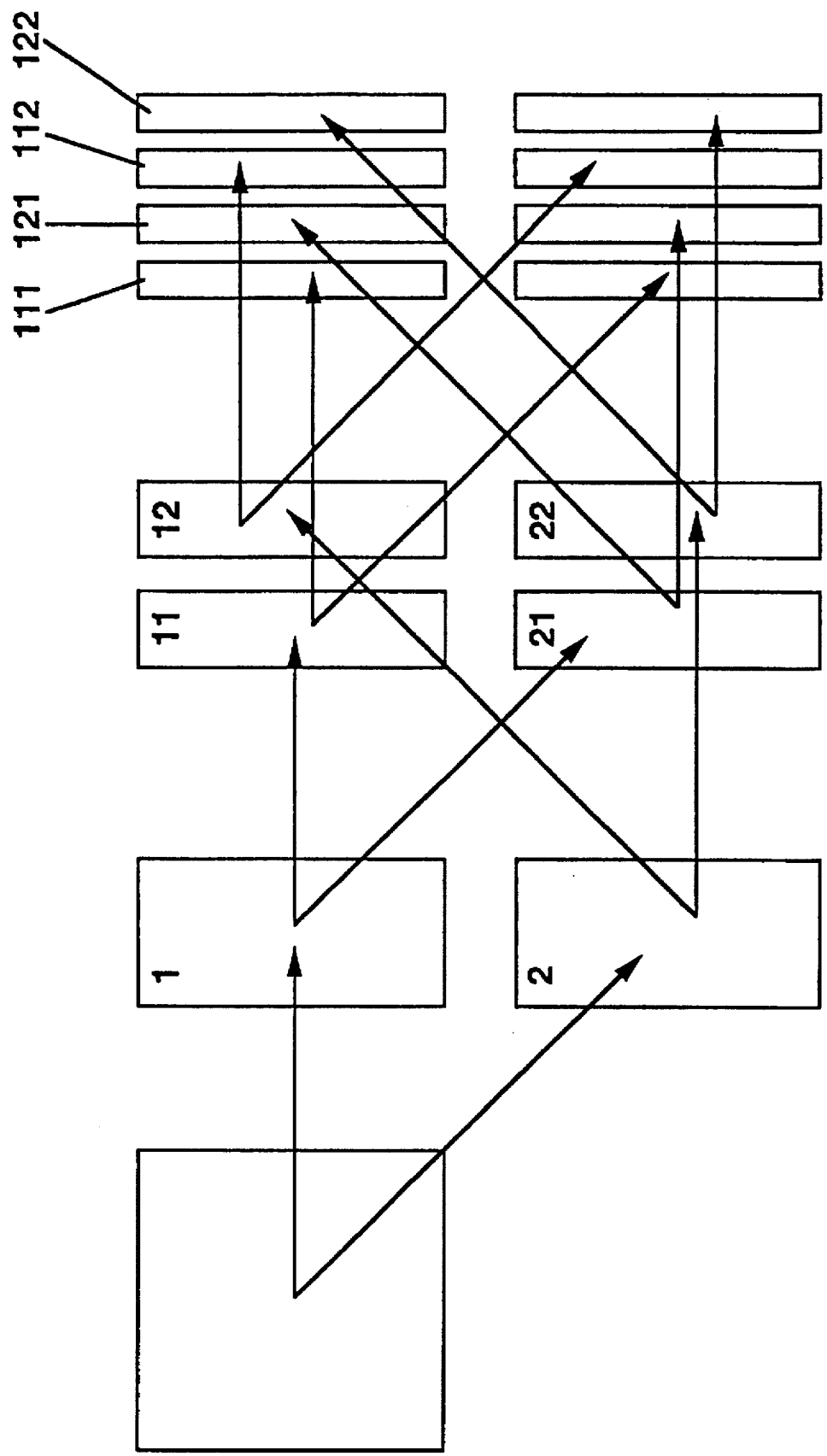

United States Patent [19]

Lebl

[11] Patent Number: 5,688,696
[45] Date of Patent: Nov. 18, 1997

[54] COMBINATORIAL LIBRARIES HAVING A PREDETERMINED FREQUENCY OF EACH SPECIES OF TEST COMPOUND

[75] Inventor: Michal Lebl, Oro Valley, Ariz.

[73] Assignee: Selectide Corporation, Tucson, Ariz.

[21] Appl. No.: 354,199

[22] Filed: Dec. 12, 1994

[51] Int. Cl.$^6$ .................. G01N 33/531; G01N 33/543
[52] U.S. Cl. ..................... 436/518; 435/6; 435/7.1; 436/501; 436/528; 436/529; 436/530; 436/531; 436/543; 530/333; 530/334
[58] Field of Search ............... 435/6, 7.1; 436/501, 436/518, 528, 529, 530, 531, 543; 530/333, 334; 536/18.5, 25.3

[56] References Cited

FOREIGN PATENT DOCUMENTS

WO 92/00091  1/1992  WIPO.
WO 93/24517  12/1993  WIPO.

OTHER PUBLICATIONS

Needels et al "Generation and Screening of an oligonucleotide–encoded synthetic peptide library" PNAS vol. 90 pp. 10700–10704 (1993).
Barrett et al., 1992, Anal. Biochem. 204: 357.
Bray et al., 1994, J. Organic Chem. 59: 2197.
Burgess et al., 1994, J. Med. Chem. 37: 2985.
Cwirla et al., 1990, Proc. Natl. Acad. Sci. USA 87: 6378–6382.
Eichler and Houghten, 1993, Biochemistry 32:11035.
Frank, 1993, Bioorganic and Medicinal Chemistry Letters 3:425.
Frank and Doring, 1988, Tetrahedron 44: 6031.
Frank, 1992, Tetrahedron 48: 9217.
Furka et al., 1991, Int. J. Peptide Protein Research 37: 487.
Furka et al., 1980, 14th International Congress of Biochemistry, Prague.
Furka, et al., 1988, X$^{th}$ International Symposium on Medicinal Chemistry, Budapest, 1988.
Gallop et al., 1994, J. Med. Chem. 37:1233.
Geysen et al., 1986, Molecular Immunology 23: 709.
Gordon et al., 1994, J Med Chem 37:1385.
Houghten et al., 1991, Nature 354: 84–86.
Jung and Beck–Sickinger, 1992, Angew Chem Int Ed Engl 31:367.
Kerr et al., 1993, J. Am. Chem. Soc. 115:2529.
King et al., 1990, Int. J. Peptide Protein Res. 36: 255–266.
Krchnak and Vagner et al., 1988, Collect. Czech. Chem. Commun. 53:2542–2548.
Krchnak and Vagner, 1990, Peptide Research 3:182.
Lam et al., 1993, Bioorg. Med. Chem. Lett. 3: 419.
Lam et al., 1991, Nature 354:82.
Lam and Lebl, 1992, Immunomethods 3: 11–15.
Lebl et al., 1992, in C.h Schneider and A.N. Eberle, Eds., Peptides: 67–69.
Moran et al. 1995, Angew. Chem. Int. Ed. Engl. 34: 2287–2291.
Nikolaiev et al., 1993, Peptide Res. 6: 161–170.
Ohlmeyer et al., 1993, Proc. Natl. Acad. Sci. USA 90: 10922.
Pinilla et al., 1992, Biotechniques 13:901.
Salmon et al., 1993, Proc. Natl. Acad. Sci. USA 90: 11708.
Speth et al., 1989, Peptide Research 2: 232–237.
Stankova et al., 1994, Drug Development Research 33: 146–156.
Bray et al., 1993, Tetrahedron Letters, 34:4411–4414.
Campian et al., 1993, 13th APS Edmonton, Canada.
Daniels et al., 1989, Tetrahedron Letters 30:4345–4348.
Devlin et al., 1990, Science 249:404–406.
Eichler et al., 1991, Peptide Research 4:296–307.
Lebl and Eichler, 1989, Peptide Research 2:232–235.
McLafferty et al., 1993, Gene 128:29–36.
Merrifield, 1963, J. Am. Chem. Soc. 85:2149–2154.
Pinilla et al., Gene 128:71–76.

Primary Examiner—Lora M. Green
Attorney, Agent, or Firm—Pennie & Edmonds

[57] ABSTRACT

A technique for generating nonrandom combinatorial libraries on solid phase supports in which each of a set of predetermined species of test compounds is present on a predetermined number of solid phase supports, preferably on only one, and each solid phase support has only a single species of test compound. Each of the predetermined species of test compounds is prepared with absolute certainty because the technique does not employ any random division of the solid phase supports. Rather, the method is based on the stepwise division of a continuous solid phase support matrix prior to each synthetic step in which more than one type of subunit is added. Non-limiting examples of matrices of the solid phase supports include polypropylene membranes, polytetrafluoropropylene membranes and cotton thread. The combinatorial libraries made by the technique are also disclosed.

30 Claims, 3 Drawing Sheets

5,688,696

COMBINATORIAL LIBRARIES HAVING A PREDETERMINED FREQUENCY OF EACH SPECIES OF TEST COMPOUND

1. FIELD OF THE INVENTION

The present invention concerns the field of combinatorial libraries of species of test compound that are synthesized on solid phase supports. A combinatorial library is a collection of multiple species of chemical compounds that consist of randomly selected subunits. Such libraries are useful because they can be screened to identify a ligand for an acceptor of interest. More particularly the invention concerns methods for constructing such libraries when the solid phase support is a material that can be readily fashioned into further divisible pieces.

2. BACKGROUND OF THE INVENTION

Techniques in combinatorial chemistry are gaining wide acceptance among modern methods for the generation of new pharmaceutical leads (Gallop, M. A. et al., 1994, J. Med. Chem. 37:1233–1251; Gordon, E. M. et al., 1994, J. Med. Chem. 37:1385–1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82–84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc.Natl.Acad.Sci. USA 90:11708–11712), or by reading its code (Kerr, J. M. et al., 1993, J.Am.Chem.Soc. 115:2529–2531; Nikolaiev, V. et al., 1993, Pept. Res. 6:161–170; Ohlmeyer, M. H. J. et al., 1993, Proc.Natl.Acad.Sci.USA 90:10922–10926).

Soluble random combinatorial libraries can be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487–493). The construction of soluble libraries for iterative screening have also been described (Houghten, R. A. et al.1991, Nature 354:84–86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82–84).

When random combinatorial libraries are synthesized, however, representation of all possible structures can be achieved with near certainty only in cases in which the number of particles used for the synthesis is at least an order of magnitude higher than the number of synthesized structures (Burgess, K. et al., 1994, J. Med. Chem. 37:2985–2987).

For library construction, it would be desirable to perform the synthesis on a defined number of solid phase particles exactly matching the number of compounds of which the library is composed. This number is, generally, the product of the number of number of types of subunits at each of the predetermined number of "randomized" positions. For example, a library of three positions (trimers) in which each position can be occupied by one of five types of subunit has 5×5×5=125 species. With this ideal situation, we would be able to eliminate the statistical uncertainty of library generation by the split and mix procedure. An assay of the library might then be performed without "missing" an active compound or detecting the identical structure several times, which would be especially advantageous in the case of small libraries (the range of tens of thousands structures), where it is not unusual to find only single active compound (see e.g. (Stankova, M. et al., 1994, Drug. Develop. Res. 33:146–156)). Thus, there is a need in the art of synthesizing combinatorial libraries of a method to synthesize a library having each of the potential species of the library a predetermined number of times, preferably once.

3. SUMMARY OF THE INVENTION

The present invention encompasses a method of making a combinatorial library on a solid phase support, the matrix of which can be readily and continuously fashioned into separate pieces by cutting. The test compounds of a combinatorial library are comprised of subunits at various positions. The species of test compounds of the combinatorial library are synthesized by the stepwise addition of subunits at each position of the test compound. The subunits are selected from a set of types of subunits for that position. According to the invention, prior to each stepwise addition, the support matrix is divided into a number of pieces which is equal to the number of types of subunits to be added at that step. This process can be performed repetitively until the piece of support matrix becomes impractically small.

Following the method of the invention, the practitioner can construct a combinatorial library having a predetermined number of species and a predetermined number of pieces of solid phase supports. In the library there is only a single species of test compound attached to any single piece of solid support. A library constructed according to the invention contains each of the predetermined species of test compounds on a predetermined number of pieces of solid phase support. In a preferred embodiment, each species will be present on one and only one support.

The present invention differs from the previously employed methods of synthesizing combinatorial libraries because the method of the present invention employs a predetermined scheme of division to replace the steps of mixing and random reassortment. These libraries are thus termed "nonrandom" or "directed" libraries.

The methods of division can be devised so that the resultant pieces are grossly recognizable, e.g., having different lengths, widths or, in the case wherein the pieces are planar, the pieces can be fashioned to have distinct shapes of their sides and ends. By coordination of the stepwise addition of the type of subunit and the gross characteristics of the supports, the type of subunit can be identified.

4. BRIEF DESCRIPTION OF THE FIGURES

FIG. 1: General scheme for the synthesis of directed libraries. Example of the library with three positions randomized by two amino acids in each step, generating the library of eight tripeptides. Row 1 depicts the coupling of amino acid #1. Row 2 depicts the coupling of amino acid #2. Column 2 depicts the 1st coupling. Column 3 depicts the 2nd coupling. Column 4 depicts the 3rd coupling.

Figure 2:
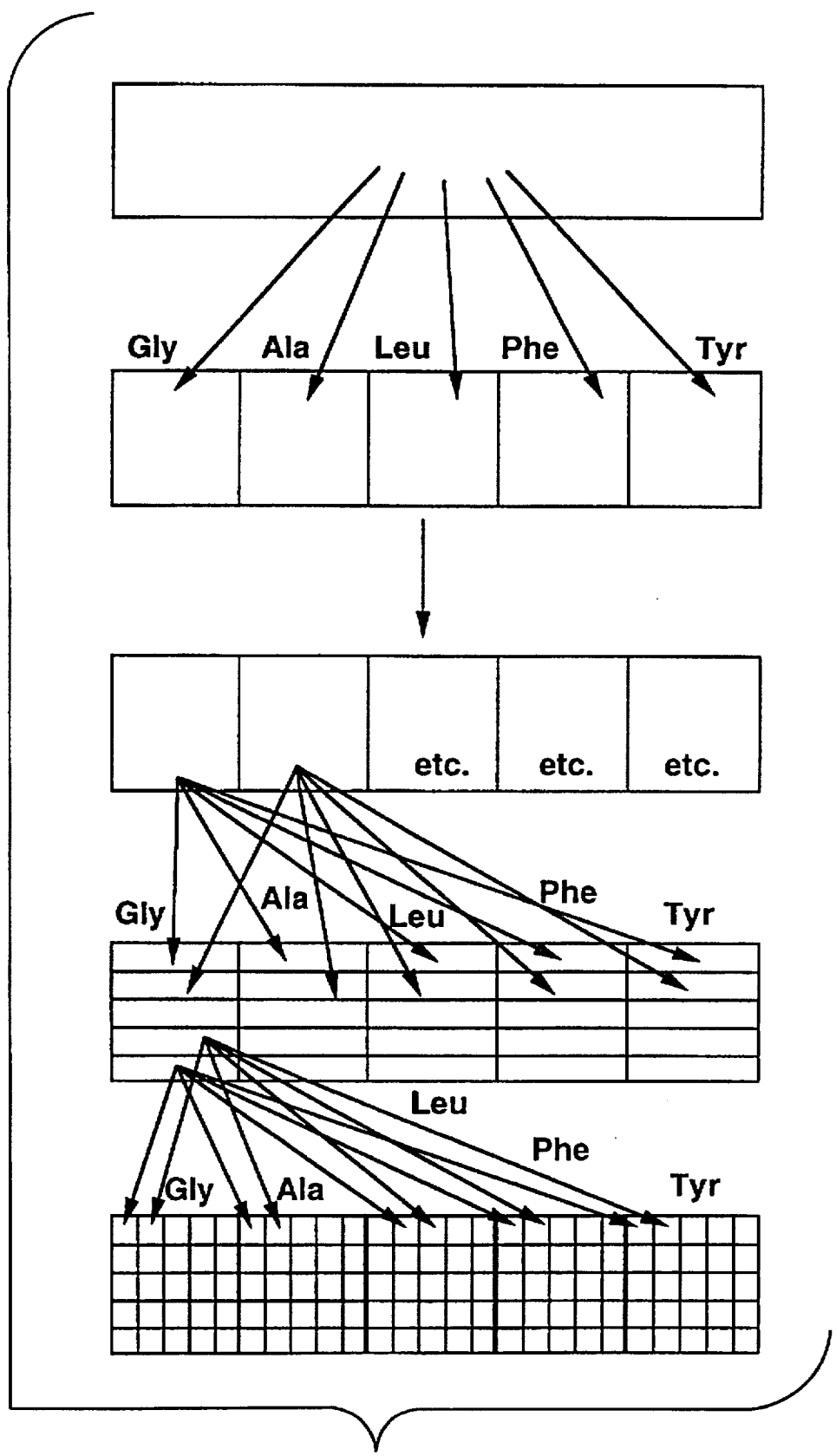

FIG. 2: Scheme of the synthesis of model library of 125 tetrapeptide mixtures on cotton string. Steps 1–4 involve coupling. Step 3 involves coupling a mixture of L-amino acids to all pieces of thread.

Figure 3:
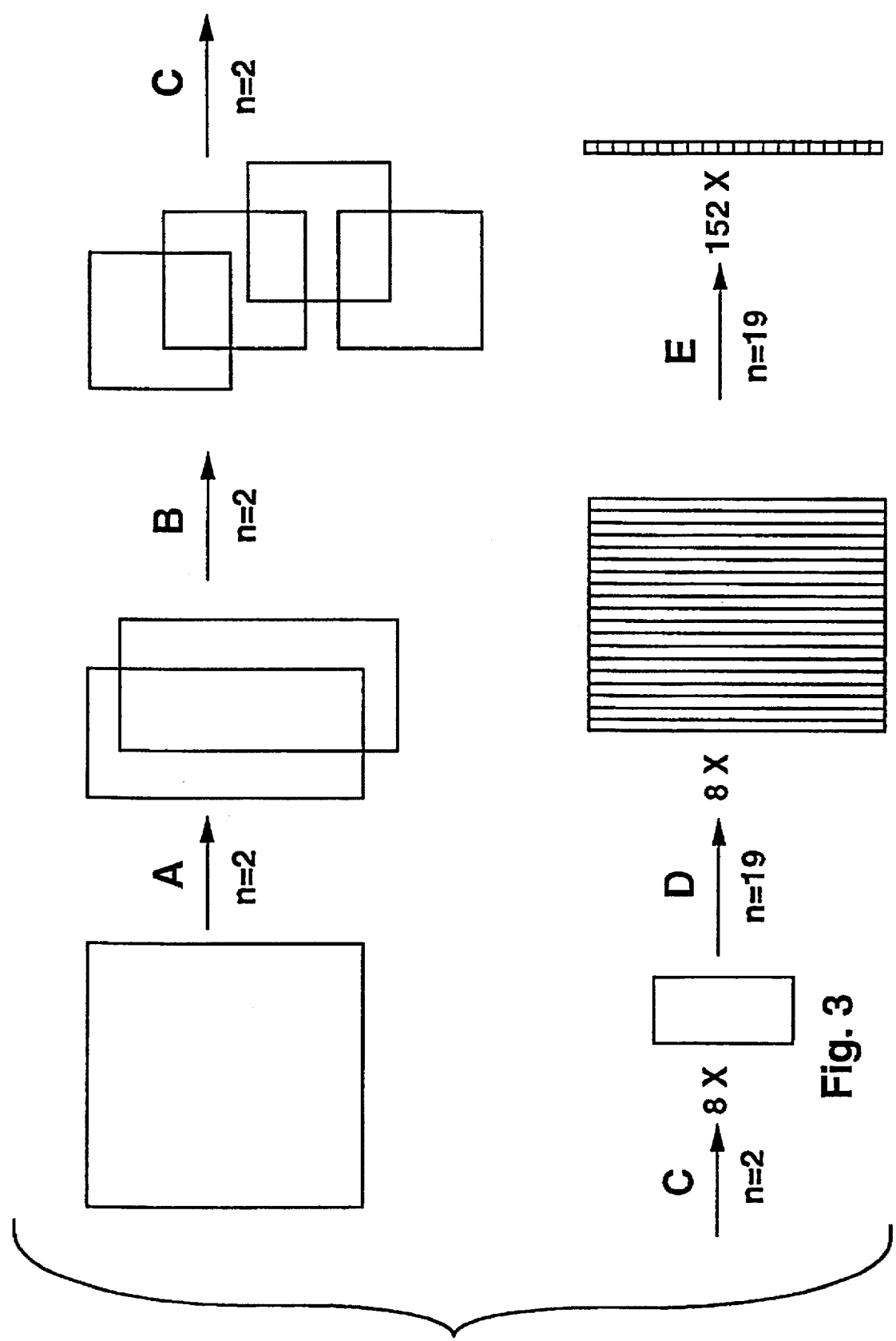

FIG. 3: Scheme of the synthesis of membrane library of 2888 pentapeptides. "n"=Number of amino acids randomized in the particular position.

5. DETAILED DESCRIPTION OF THE INVENTION

As used herein a species of test compound can be a single defined molecular structure. Alternatively, a species of test compound can be a motif species, which is a mixture of defined molecules wherein multiple species of subunits are present at one Or more of the positions of the species of test compound. Motif libraries are combinatorial libraries wherein the species of test compounds are motif species. As used herein, when motif libraries are constructed, the term "type of subunit" refers either to a chemical species of subunit or to a defined mixture of species of subunits. Regarding a motif library, the position of a species of test compound wherein a mixture of species of subunits has been added is called a "mixed position". In keeping with the nomenclature of random combinatorial libraries, the position of a species of test compound of a motif library or a nonmotif library wherein a single species of subunit is present is called a "random position", except when all species of the library have the same species of subunit at a given position, in which case that position is called an invariant or a fixed position. Motif libraries are described in co-pending, commonly assigned patent application Ser. No. 08/246,435 filed May 20, 1994, which is hereby incorporated by reference.

To permit the synthesis of the species of test compound attached to the support matrix, a linking means is provided. The linking means can have multiple reactive sites for attachment of subunits. In one embodiment the subunits are bifunctional subunits having removable protecting groups; amino acids are the familiar example. Under these circumstances the test compounds are polymers.

In an alternative embodiment the linking means comprise multiple, orthogonally blocked reactive sites, and are termed scaffolds. In this embodiment, the subunits provide substituents of the scaffold. Thus, the species of test compounds are species of substituted scaffolds. The subunit added at each site of the scaffold can be bifunctional or monofunctional and the substituent attached to a reactive site of the scaffold can be comprised of one or more subunits.

According to the invention the bifunctional and monofunctional subunits of a library of substituted scaffolds and the bifunctional subunits of a library of polymers can be joined to the growing test compound by a variety of chemical bonds of which the following are non-limiting examples: amide, ester, urea, urethane, carbon-carbonyl bonds, carbon-nitrogen bonds, carbon-carbon single bonds, olefine bonds, thioether bonds, and disulfide bonds. The chemistries of the production of test compounds in scaffold and non-peptide polymer libraries are described in co-pending commonly assigned patent application Ser. No. 08/249,830, filed May 24, 1994, which is hereby incorporated by reference.

Solid phase synthesis of peptides is normally performed on a beaded polymer (Merrifield, R. B., 1963, J.Am.Chem.Soc. 85:2149–2154), however, alternative forms of solid support can be employed. The solid supports include membranes (Daniels, S. B. et al., 1989, Tetrahedron Lett. 30:4345–4348), sheets of paper (Frank, R., 1992, Tetrahedron 48:9217–9232; Frank, R. and R. Döring, 1988, Tetrahedron 44:6031–6040), or cotton (Eichler, J. and R. A. Houghten, 1993, Biochemistry 32:11035–11041; Lebl, M. and J. Eichler, 1989, Pept. Res. 2:232–235). For the review of multiple synthetic techniques see (Frank, R., 1993, Bioorg. Med. Chem. Lett. 3:425–430; Jung, G. and A. G. Beck-Sickinger, 1992, Angew. Chem. Int. Ed. Engl. 31:367–383). Prior experience with cotton (Eichler, J. et al., 1991, Pept. Res. 4:296–307) led to the selection of cotton threads as one experimental solid support for the synthesis of "directed" or "nonrandom" libraries. The principle of such libraries is simple and is illustrated in FIG. 1. The continuous support is divided into as many parts as the number of types of subunits utilized in the first randomization step, and the pieces are individually reacted with the appropriate residue. After completion of the reaction, each fragment of the support matrix is then divided into as many parts as the number of types of subunits used in the second randomization step, with the appropriate pieces from each fragment pooled for coupling.

In this manner, the synthesis can continue until subunits are added at all the positions of the test compound or until the mechanical limit of handling the support is reached. The convenient mechanical limit of cotton thread is achieved at a dimension of several millimeters, which defines the practical capacity of a library of cotton thread at between 10 test compounds to 50,000 test compounds. Libraries of these proportions are of substantial value, especially in the case of nonpeptidic libraries. Thus, libraries having as few as two, three, four and five random positions for which the number of types of subunits can be between 2 or 3 and 19 or more are within the scope of the invention.

In an alternative embodiment the matrix can be a functionalized membranes. Non-limiting examples of a suitable support matrix include polypropylene and polytetrafluoroethylene TEFLON The smallest practical area is about 1 $mm^2$ and since the membrane is only 10 μm thick, a library of several million compounds can be constructed most readily when automation of this process is employed. The size of a library constructed using a membraneous support matrix is limited only by considerations of economy, efficiency and the expense of screening the library and not by any technical considerations of its synthesis.

A third embodiment of the invention is a "restructurable toothbrush" having bunches of threads of functionalized material with better mechanical properties than cotton. The bunches of threads from different brushes can be disassembled and reassembled in different combination for the next stepwise addition of subunits. The individual bunches of threads can be disassembled after two or three rounds of step wise addition and recombined for the next step. For the last randomization step the threads can be cut into pieces according to the above-described method of the invention.

The disclosed method for the construction of 'directed' libraries allows for the incorporation of simple coding schemes, that employ simple (i.e., grossly visual) identification of important structural features in the library, based on the physical characteristics of the support, such as the color (Campian, E. et al., 1993, 13th APS, Edmonton, Canada) size and shape of the material (length in the case of thread).

In constrast to libraries the species of which are constructed in a fixed array, wherein the position of each species identifies its structure, in the preferred embodiments of the present invention the complete structure of a species of test compound is not encoded by a grossly observable characteristic. Rather, the structures of the species of test compounds selected after the screening test are determined by structural analysis. The structural analysis can be conducted by using such techniques as Edman degradation, in the case of peptide test compounds, or mass spectroscopy. The structure which is analyzed can be the test compound itself or the structure can be an encoding molecule which is attached to each solid phase support in addition to the test compound. The structures of the encoding molecules attached to a solid phase support are, firstly, arbitrarily and systematically related to the species of the test compound attached to the support so as to identify the test compound and, secondly, selected so as to be readily determinable. The selection and use of arbitrary coding molecules in combinatorial libraries is described in co-pending commonly assigned patent application Ser. No. 08/249,830, filed May 24, 1994, which is hereby incorporated by reference.

6. EXAMPLES

The following examples are provided as illustrative examples of certain embodiments of the invention and are not intended as a limitation on the scope of the present invention.

We have prepared two model "nonrandom" peptide libraries. The preparation and screening of each of these libraries is first summarized briefly below. A more detailed description of the materials and methods, the synthesis and screening of each of these two libraries follows in Sections 6.1–6.5.

The first library was prepared on cotton thread and contained only 125 peptide mixtures (see FIG. 2). Cotton thread (125 cm) was modified by beta alanine (Eichler, J. et al., 1991, Pept. Res. 4:296–307) and glycine was attached to it. The thread was then divided into five pieces and Gly, Ala, Leu, Phe, and Tyr were coupled to each piece, respectively. After complete coupling and Fmoc deprotection, a mixture of L-amino acids was coupled to every thread. Thereafter, for two successive steps, each thread fragment was sectioned into 5 pieces and each piece was acylated with one amino acid selected the above-noted set of five amino acids. Thereafter the resultant 125 fragments were combined, deprotected, neutralized, washed and dried; resulting in the generation of a motif library of 125 tetrapeptide motif species (mixtures of 19 species of peptides on each particle having positions 1, 2 and 4 as random positions and position 3 as a mixed position).

Each piece was then cut in half and both halves were placed into two matching microtiter plates, one of them equipped with a filter. The filter plate was then exposed to ammonia gas in a desiccator to release the peptides from the cotton. Gas ammonolytical cleavage, described earlier (Bray, A. M. et al., 1994, J.Org.Chem. 59:2197–2203; Bray, A. M. et al., 1993, Tetrahedron Lett. 34:4411–4414), was chosen as a cleavage method because, after cleavage, the peptide remains on the surface of the dry support particle. The peptides can be dissolved into the testing buffer.

After extraction of the peptide with buffer, the peptide was transferred to another plate and an anti-β-endorphin antibodies binding assay was performed. One well was observed to react positively, and sequencing of the corresponding cotton fraction, identified the sequence Tyr-Gly-Mix-Phe (Mix is a mixture of all amino acids), corresponding to the known motif for anti-β-endorphin antibodies. Further analysis revealed that a one centimeter of cotton thread can yield 400 nmol of released peptide, allowing for the preparation of 40 ml of a 10 μM solution of test compound, more than enough for multiple assays.

The second example was a 2888 peptide library, which was synthesized using a 16×16 cm sheet of functionalized polytetrafluoroethylene ("TEFLON") membrane. The membrane was acylated by a N-protected β-alanine, and a linker composed of a repeated sequence of β-alanine and glycine was constructed. The scheme of synthesis is given in FIG. 3. The species of test compounds of the library had the structure Xxx-Xxx-Pro/Gly-Gln/Phe-Phe/Leu (Xxx is one of 19 L amino acids used for the randomization), which contained one copy of the sequence Leu-His-Pro-Gln-Phe (38 copies of Xxx-His-Pro-Gln-Xxx), with His-Pro-Gin being the known motif for streptavidin, and one copy of Tyr-Gly-Gly-Phe-Leu, containing Tyr-Gly-Xxx-Phe sequence, the known motif for an anti-β-endorphin monoclonal antibody (Barrett, R. W. et al., 1992, Anal. Biochem. 204:357–364; Cwirla, S. E. et al., 1990, Proc.Natl.Acad-.Sci.USA 87:6378–6382; Devlin, J. J. et al., 1990, Science 249:404–40625; Lam, K. S. et al., 1993, Bioorg. Med. Chem. Lett. 3:419–424; Lam, K. S. et al., 1991, Nature 354:82–84; McLafferty, M. A., 1993, Gene 128:29–36; Pinilla, C., 1993, Gene 128:71–76). The library was then screened with two model targets, streptavidin and anti-β-endorphin, using the solid phase binding protocol.

Screening with streptavidin yielded 55 positive squares. The specificity of the peptides was determined by addition of the known competitor biotin. Seventeen of the squares contained peptides that did not react with streptavidin in the presence of biotin, however, all 17 of the squares again stained positively in the absence of biotin with approximately equal intensity. The peptides on three squares were sequenced individually with the results given in Table 1. Small pieces of all squares were cut and sequenced at once. This multiple sequencing experiment (Lebl, M. et al., 1993, In C. H. Schneider and A. N. Eberle, Peptides 1992, Proc.22.EPS Eds. ESCOM, Leiden) revealed the requirements of individual positions of the peptide chain.

Incubation with anti-β-endorphin provided 21 stained squares. These positively interacting particles were destained, and reincubated with anti-β-endorphin antibody using alternative detection scheme. In the first staining the antibody was labelled by biotin and detection of bound target was achieved by incubation with streptavidin-alkaline phosphatase complex. The second round of detection was performed by incubation with anti-mouse antibody-alkaline phosphatase complex. In this way the nonspecific interactions of the first detection scheme were eliminated and since the second detection was done only with selected particles, the probability of detecting the nonspecific interactions (specific interactions of the detection system) was significantly decreased. The second incubation detected only three positive squares. They were sequenced and sequences found are given in Table 1. Predicted sequences with the motif Tyr-Gly-__-Phe were found.

TABLE 1

| Sequences found on positive squares selected for binding to streptavidin and anti-β-endorphin | |
|---|---|
| Streptavidin | Anti-β-endorphin |
| Gly—His—Pro—Gln—Phe | Tyr—Gly—Gly—Phe—Leu |
| Met—His—Pro—Gln—Phe | Tyr—Gly—Gly—Phe—Phe |
| Lys—His—Pro—Gln—Phe | Tyr—Gly—Pro—Phe—Leu |

6.1. MATERIALS AND METHODS

Instrumentation: UV/VIS absorption spectra were recorded on a Hewlett Packard HP 8452A Diode-Array spectrophotometer using a 1 cm quartz cuvette. Sequencing by Edman degradation was performed on an ABI 4778 protein sequencer (Applied Biosystems, Foster City, Calif.) and Porton PI 3010 instrument (Porton Instruments, Tarzana, Calif.).

Materials: Commercial-grade solvents were used without further purification. Protected amino acids were obtained from Bachem (Torrance, Calif.), Advanced ChemTech (Louisville, Ky.), or Propeptide (Vert-le-Petit, France). Monoclonal anti-β-endorphin antibodies (clone 3-E7) were purchased from Boehringer Mannheim. Streptavidin conjugated to alkaline phosphatase was obtained from Pierce (Rockford, Ill.), and the goat-anti-mouse alkaline phosphatase complex was obtained from Bio-Rad (Richmond, Calif.). d-Biotin was purchased from Sigma (St. Louis, Mo.).

General Procedures: Solid phase synthesis was performed manually in polypropylene syringes (Krchňák, V. and J. V ágner, 1990, Pept. Res. 3:182–193). Fmoc protecting groups were cleaved with 50% piperidine/DMF for 1×10 min. DIC in DMF was used for the activation of Nα-Fmoc amino acids. The completeness of each condensation reaction was monitored by the bromophenol blue method (Krchňák, V. et al., 1988, Collect.Czech.Chem.Commun. 53:2542–2548). The coupling protocol included washing with DMF (6–8 times) between coupling and deprotection and between deprotection and coupling. Final deprotection was done by mixture K (King, D. S. et al., 1990, Int. J. Peptide Protein Res. 36:255–266).

6.2. SYNTHESIS OF THE DIRECTED LIBRARY ON COTTON STRING

Cotton string (5 m, 6 m/g) was treated for 1 h in 25% trifluoroacetic acid (TFA) in dichloromethane (DCM). It was washed by DCM (3x), neutralized by 5% diisopropylethylamine in DCM (5 min) and washed by DCM and DMF (3x). Fmoc-β-Ala (2 mmol) was coupled overnight by DIC (2 mmol) and HOBt (2 mmol) activation with addition of N-methylimidazole (3.5 mmol). Cotton was washed by DMF and substitution was determined by photometrical determination of cleaved Fmoc group—0.41 mmol/g (683 nmol/cm). Five pieces of the cotton string (25 cm each) were placed into five polypropylene syringes and Fmoc protected amino acids (Phe, Tyr(But), Ala, Leu, Gly) were coupled by DIC/HOBt protocol. After coupling completion (monitored by bromophenol blue method), the strings were washed by DMF, placed in one syringe and Fmoc group was cleaved. After washing with DMF and 2% solution of HOBt in DMF the mixture of 19 L (cysteine excluded) Fmoc amino acids with molar ratio (determined in pilot experiments) adjusted for different reactivities (Eichler, J. and R. A. Houghten, 1993, Biochemistry 32:11035–11041; Geysen, H. M. et al., 1986, Mol. Immun. 23:709–715; Pinilla, C. et al;, 1992, BioTechniques 13:901–905) was coupled to all cotton pieces. After completion of this coupling the cotton was washed, Fmoc group was cleaved and washed cotton string was divided into five syringes in the following way. From each string five cm of the cotton was cut and placed in the different syringe. In this way all syringes have only one 5 cm piece of cotton cut from each 25 cm string and none have more than one. Coupling of five amino acid derivatives (same as above) was performed, cotton was washed, Fmoc group was removed and cotton was subdivided again. In this case 1 cm pieces were cut from all 5 cm pieces and placed in five syringes. Coupling of the same five amino acids was performed, Fmoc group was cleaved and side chain protecting group were cleaved by mixture of TFA, DCM and anisole (50:45:5) for 2 h. Cotton pieces were washed by DCM, MeOH and dried. Quantitative amino acid analysis of a sample of one string revealed the substitution of 400 nmol/cm.

6.3. SCREENING OF THE DIRECTED LIBRARY ON COTTON

Cotton pieces were cut in half and placed into matching positions of the two matching microtiter plates (one equipped with a filter bottom and one regular plate—"structure evaluation plate"). Filter plate was placed into the desiccator which was repeatedly evacuated and filled with gas ammonia. After 20 h exposure to ammonia the desiccator was evacuated and ammonia removed. Release buffer PBS/Tween was added to each well (100 µl) and plates were shaken overnight at room temperature. Solution was filtered to the test plates.

For the inhibition ELISA, 96-well Immulon plates (Dynatech) were used. Each well was initially coated with 50 µl of streptavidin (20 µg/ml) in bicarbonate buffer (pH 9.4) (Pierce) overnight, followed by three washes with PBS. Wells were treated with 200 µl of bovine serum albumin (BSA, 3 mg/ml) in PBS to prevent nonspecific adsorption and washed three times with PBS/Tween, and 50 µl of biotinylated Tyr-Gly-Gly-Phe-Leu (Salmon, S. E. et al., 1993, Proc.Natl.Acad.Sci.USA 90:11708–11712) (10 ng/ml) was added. After 1 hr, plates were washed with PBS/Tween, and 50 µl of solution released from cotton pieces (or Tyr-Gly-Gly-Phe-Leu, positive control) was added, followed by 50 µl of anti-β-endorphin (40 ng/ml). After 1 hr of incubation at room temperature, plates were washed with PBS/Tween, and 50 µl of a 1:1000 dilution of goat anti-mouse IgG horseradish peroxidase conjugate (Bio-Rad) was added. One hour later, the plates were washed, and 100 µl of solution of 30 µl of 30% $H_2O_2$ in 10 ml of 2,2'-azidobis(3-ethylbenzthiazolinesulfonic acid) substrate in citrate buffer (pH 4.2) was added. Fifteen minutes later, the ELISA plates were read at 405 nm. Only one well has shown significant inhibition. Sample of the cotton piece (0.3 mm) from the matching well in the "structure evaluation plate" was sequenced and sequence Tyr-Gly-Mix-Phe was found.

6.4. SYNTHESIS OF THE DIRECTED LIBRARY ON FUNCTIONALIZED CROSSLINKED TEFLON MEMBRANE

Hydrophilic aminopropyl functionalized membrane (UV crosslinked aminopropyl methacrylamide, N,N-dimethylacrylamide and methylene-bis-acrylamide on TEFLON membrane, 16×16 cm, Perseptive Biosystems, Bedford, Mass.) with approximate 35 nmol/$cm^2$ substitution was placed into 50 mL Falcon tube and acylated by Fmoc-β-Ala using DIC/HOBt procedure in DMF. Fmoc-Gly, Fmoc-β-Ala, and Fmoc-Gly were coupled consecutively. After deprotection the membrane was divided into two parts and Fmoc-Phe and Fmoc-Leu were coupled to them, respectively. After coupling completion (bromophenol blue monitoring) and deprotection, the pieces were divided again into two halves and recombined for the coupling of Fmoc-Gln and Fmoc-Phe. For the next coupling the membrane was divided again into two pieces and recombined for coupling of Fmoc-Pro and Fmo-Gly. The pieces resulting from these couplings (8×4 cm) were now divided into 19 strips (8×0.21 cm) and the strips were placed into 19 small polypropylene tubes. Nineteen natural amino acids (excluding Cys) were used for coupling in this stage. After coupling completion and Fmoc deprotection, The strips were cut into 19 pieces (4×2.1 mm) and divided into 19 vessels again. The same set of 19 Fmoc amino acids was used for the last coupling. All pieces were combined, Fmoc group was removed and side chain protecting groups were cleaved by mixture K (King, D. S. et al., 1990, Int. J. Peptide Protein Res. 36:255–266). Membrane pieces were washed by TFA (2x), DCM (5x), MeOH (3x), water (5x). Substitution based on measurement of the absorbance of the last Fmoc release was 43.3 nmol/cm$^2$.

6.5. SCREENING OF THE DIRECTED LIBRARY ON CROSSLINKED TEFLON MEMBRANE

The peptide library was screened according to published protocol (Lam, K. S. and M. Lebl, 1992, Immunomethods 1:11–15). The peptide squares were first washed with double-distilled water. After thorough washing, the squares were washed and coated with 0.05% gelatin (w/v) to block nonspecific binding. Washing with PBS/Tween (137 mM NaCl, 2.7 mM KCl, 4.3 Na$_2$HPO$_4$, 1.4 mM KH$_2$PO$_4$, pH 7.2 with 0.1% Tween-20) and 2xPBS/Tween/gelatin (2x PBS, 0.1% Tween-20 (v/v), and 0.05% gelatin (w/v)) was followed by an incubation with a 20 nM streptavidin-alkaline phosphatase in 2x PBS/Tween/gelatin. Again the library was washed with PBS/Tween, 2xPBS/Tween/gelatin and with TBS (137 mM NaCl, 2.7 mM KCl, 25 mM Tris base, pH 7.4). The standard substrate 5-bromo-4-chloro-3-indolyl phosphate was added then added. The library and substrate were then transferred to petri dishes for color development. Fifty-five color squares were collected, washed with 6M guanidine hydrochloride, pH 1.0, decolorized with DMF, gelatin coated and competed with 100 nM d-Biotin with 20 nM steptavidin-AP in 2xPBS/Tween/gelatin. Incubation with substrate yielded 17 colorless, competed squares. Reincubation with 20 nM streptavidin-AP produced 17 positively reacting squares following treatment with substrate.

The remaining library was then recycled with 6M guanidine hydrochloride, pH1.0, DMF, and gelatin coated. After washing with PBS/Tween and 2xPBS/Tween/gelatin, 250 ng/ml biotinylated anti-β-endorphin antibody in 2xPBS/Tween/gelatin was added. Following thorough washing, streptavidin-alkaline phosphatase was added. The library was then washed, substrate was added, and color development proceeded as described above. Twenty one squares developed color, and subsequent recycling prepared them for specificity determination. Using 2xPBS/Tween/gelatin as the buffer, 200 ng/ml anti-β-endorphin antibody was added, and thorough washing was followed with 1.5 nM goat-anti-mouse-AP. The squares were then washed with PBS/Tween, 2xPBS/Tween/gelatin and TBS, and substrate was added. As a result, 3 squares developed the color that indicates binding.

I claim:

1. A method of making a combinatorial library of test compounds which comprises at least two successive iterations of the steps of:
   a) selecting a set consisting of two or more types of subunits;
   b) dividing a continuous solid phase support having a linker, said linker having reactive sites and having one or more protecting groups, into a number of physically separate pieces of support equal to an integral multiple of the number of selected types of subunits;
   c) attaching one type of subunit to substantially all the reactive sites attached to a corresponding piece of solid phase support; and thereafter
   d) removing a protecting group from the linker so that reactive sites are provided, thereby providing at least two subunits attached to each piece of solid phase support, and wherein each piece of solid phase support has a single species of test compound of selected subunits attached to it and each species of test compound is represented on a predetermined number of pieces of solid phase support.

2. The method of claim 1 wherein the linker of the solid phase support is a scaffold, said scaffold being comprised of multiple, othogonally protected reactive sites.

3. The method of claim 1 further comprising a step, following the last iteration, of releasing the attached subunits from the solid phase support.

4. The method of claim 1 wherein the solid phase support is selected from the group consisting of a membrane, a sheet of paper and cotton.

5. The method of claim 4 wherein the membrane is a functionalized crosslinked polytetrafluorethylene.

6. The method of claim 4 wherein the cotton is in the form of a string or a thread.

7. The method of claim 1 wherein the subunits have one or more protecting groups being releasable independently of at least one of the protecting groups of the linker.

8. The method of claim 1 wherein the number of pieces of support in step (b) is equal to the number of selected types of subunits, so that each species of test compound is represented on exactly one piece of solid phase support.

9. A method of making a combinatorial library of test compounds which comprises the steps of:
   (a) attaching a linker having more than one protecting groups to a continuous solid phase support; and
   (b) removing one type of protecting group from the linker so that reactive sites are provided;

and further comprising at least two successive iterations of the steps of:
   (c) selecting a set consisting of two or more types of subunits;
   (d) dividing the continuous solid phase support into a number of physically separate pieces of support equal to an integral multiple of the number of selected types of subunits;
   (e) attaching one type of subunit to substantially all the reactive sites attached to a corresponding piece of solid phase support; and thereafter
   (f) removing a protecting group from the linker so that reactive sites are provided, thereby providing at least two subunits attached to each piece of solid phase support, and wherein each piece of solid phase support has a single species of test compound of selected subunits attached to it and each species of test compound is represented on a predetermined number of pieces of solid phase support.

10. The method of claim 9 wherein the linker of the solid phase support is a scaffold, said scaffold being comprised of multiple, othogonally protected reactive sites.

11. The method of claim 9 wherein the subunit is a bifunctional subunit and the protecting group is a substituent of the subunit.

12. The method of claim 11 wherein the bifunctional subunit is an amino acid.

13. The method of claim 9 further comprising a step, following the last iteration, of releasing the attached subunits from the solid phase support.

14. The method of claim 9 wherein the solid phase support is selected from the group consisting of a membrane, a sheet of paper and cotton.

15. The method of claim 14 wherein the membrane is a functionalized crosslinked polytetrafluorethylene.

16. The method of claim 14 wherein the cotton is in the form of a string or a thread.

17. The method of claim 9 wherein the subunits have one or more protecting groups releasable independently from at least one of the protecting groups of the linker.

18. The method of claim 9 wherein the number of pieces of support in step (d) is equal to the number of selected types of subunits, so that each species of test compound is represented on exactly one piece of solid phase support.

19. A method of making a combinatorial library of test compounds which comprises at least two successive iterations of the steps of:

a) selecting a set consisting of two or more types of subunits having one or more protecting groups;

b) dividing a continuous solid phase support having a linker, said linker having reactive sites, into a number of physically separate pieces of support equal to an integral multiple of the number of selected types of subunits;

c) attaching one type of subunit to substantially all the reactive sites attached to a corresponding piece of solid phase support; and thereafter d) removing a protecting group from the subunit so that reactive sites are provided, thereby providing at least two subunits attached to each piece of solid phase support, and wherein each piece of solid phase support has a single species of test compound of selected subunits attached to it and each species of test compound is represented on a predetermined number of pieces of solid phase support.

20. The method of claim 19 wherein the subunit is a bifunctional subunit and the protecting group is a substituent of the subunit.

21. The method of claim 20 wherein the bifunctional subunit is an amino acid.

22. The method of claim 19 wherein the linker has one or more protecting groups, the protecting groups of the linker being releasable independently of the protecting groups of the subunits.

23. The method of claim 19 wherein the solid phase support is selected from the group consisting of a membrane, a sheet of paper and cotton.

24. The method of claim 23 wherein the membrane is a functionalized crosslinked polytetrafluorethylene.

25. The method of claim 19 wherein the number of pieces of support in step (b) is equal to the number of selected types of subunits, so that each species of test compound is represented on exactly one piece of solid phase support.

26. A method of making a combinatorial library of test compounds which comprises the steps of:

(a) attaching a linker having one or more protecting groups to a continuous solid phase support;

(b) removing a protecting group from the linker so that reactive sites are provided;

and further comprising at least two successive iterations of the steps of:

(c) selecting a set consisting of two or more types of subunits having one or more protecting groups;

(d) dividing the continuous solid phase support into a number of physically separate pieces of support equal to an integral multiple of the number of selected types of subunits;

(e) attaching one type of subunit to substantially all the reactive sites attached to a corresponding piece of solid phase support; and thereafter (f) removing a protecting group from the subunit so that reactive sites are provided, thereby providing at least two subunits attached to each piece of solid phase support, and wherein each piece of solid phase support has a single species of test compound of selected subunits attached to it and each species of test compound is represented on a predetermined number of pieces of solid phase support.

27. The method of claim 26 wherein the linker has more than one protecting group releasable independently of the protecting groups on the subunits.

28. The method of claim 26 wherein the solid phase support is selected from the group consisting of a membrane, a sheet of paper and cotton.

29. The method of claim 28 wherein the membrane is a functionalized crosslinked polytetrafluorethylene.

30. The method of claim 26 wherein the number of pieces of support in step (d) is equal to the number of selected types of subunits, so that each species of test compound is represented on exactly one piece of solid phase support.

* * * * *